United States Patent
Buckner

(10) Patent No.: US 6,840,255 B2
(45) Date of Patent: Jan. 11, 2005

(54) ELECTRONIC DRAIN FOR WATER JACKETED INCUBATORS

(75) Inventor: Jeff Buckner, Weaverville, NC (US)

(73) Assignee: GSLE Development Corporation, Charlotte, NC (US)

( * ) Notice: Subject to any disclaimer, the term of this patent is extended or adjusted under 35 U.S.C. 154(b) by 289 days.

(21) Appl. No.: 10/274,159

(22) Filed: Oct. 21, 2002

(65) Prior Publication Data

US 2004/0074634 A1 Apr. 22, 2004

(51) Int. Cl.[7] .............................. F16K 31/02; F28F 27/00
(52) U.S. Cl. ...................... 137/1; 137/624.11; 137/340; 137/375
(58) Field of Search ................................ 137/624.11, 1, 137/334, 340, 375, 264; 165/278

(56) References Cited

U.S. PATENT DOCUMENTS

| | | | | | |
|---|---|---|---|---|---|
| 3,507,753 | A | * | 4/1970 | Jacuzzi | 202/191 |
| 4,089,662 | A | * | 5/1978 | Williams | 96/160 |
| 5,053,111 | A | * | 10/1991 | Ellerbe, Jr. | 137/391 |
| 6,062,253 | A | * | 5/2000 | Hanel et al. | 137/360 |
| 6,119,709 | A | * | 9/2000 | Kiyota | 137/1 |

* cited by examiner

*Primary Examiner*—Kevin Lee
(74) *Attorney, Agent, or Firm*—Baker & Hostetler LLP

(57) ABSTRACT

An apparatus and method is provided to evacuate liquids from a water jacket of an enclosed chamber. An electronic valve, such as a solenoid can be actuated remotely to open and allow liquids to evacuate. A controller can also be used to actuate the solenoid or at a period of time or at an event.

20 Claims, 3 Drawing Sheets

Open

Closed

ELECTRONIC DRAIN FOR WATER JACKETED INCUBATORS

FIELD OF THE INVENTION

Embodiments of the present invention generally relate to an apparatus and method for use with a controlled gas atmosphere. More particularly, the apparatus and method of the present invention relates to an electronic drain in a water jacketed incubator.

BACKGROUND OF THE INVENTION

There are a number of commercial applications that utilize a controlled gas atmosphere enclosure. For example, in the semiconductor industry, gases are injected into an enclosed chamber, wherein one of the gases is plasmarized and strikes a target on a chamber lid causing the target's materials to deposit on a wafer. Other commercial applications include using controlled gases to cultivate biological cultures in an enclosed chamber, such as an incubator.

It is desirable to maintain optimal conditions inside the incubator in order to promote the desired growth of the cultures. In a conventional incubator, gassiest such as $O_2$, $N_2$, and $CO_2$ are introduced from their respective tanks into the chamber depending on the growing conditions desired. Typically, the user sets the $CO_2$ and $O_2$ setpoints and appropriate gases are added.

Most biological incubators are either forced draft or water jacket. In the forced draft incubator, the inner space is lined with insulation instead of a water jacket. Heating of the chamber is provided by having a duct, a fan, and a heating element within the chamber. The air is typically circulated by the fan and heated by the heating element within the duct. The air is blown with more force than in the water jacket incubators in order to have more uniform circulation of the air and temperature in the chamber.

In the water jacket incubator, a water jacket surrounds the interior chamber of the incubator. FIG. 1 illustrates a conventional water jacketed incubator 100. The incubator 100 includes a cabinet 110, an interior chamber 120, a control system 160 and an outer door 150. The cabinet 110 has a set of leveling feet 145 to adjust the height or level of the incubator 100. The cabinet 110 contains a water jacket 125, (also shown in FIG. 3 at 380) which surrounds the interior chamber 120. The water jacket 125 is filled with water and is heated by a heater 155. The water in turn heats the air flow chamber (FIG. 3 at 395) where air can be circulated by air pump 175. Because water can be heated evenly, the water jacket 125 can evenly distribute the desired heat throughout the interior chamber 120. Such even heating is desired in order to provide a uniform temperature (for the biological cultures) throughout the chamber 120 and to prevent "cold spots," which can cause condensation on the inner chamber walls.

The interior chamber 120 includes a humidity pan 135 that is filled with a liquid and provides moisture for the samples that are placed on a set of shelves 130. The shelves 130 are adjustable as wells as removable. A humidity sensor 180 is provided to monitor the amount of humidity in the chamber 120 so that adjustments can be made depending on the nature of the desired culture growth. A $CO_2$ sensor 185 located in the interior chamber 120 can monitor the current $CO_2$ levels so that $CO_2$ can be replenished, as needed.

The control system 160 is provided on the cabinet 110 and includes an alarm system, a monitor system and a user interface. The outer door 150 and an inner glass door 140 provide access to the interior of the cabinet 110. The cabinet 110 has built-in sample port 175 and a front fill port 190. The front fill port 190 allows a user to fill the water jacket 125 with water or other liquids. The water can be drained at the lower portion of the cabinet 110 at a drain cap 195.

In order to drain properly, the drain cap 195 is at the lowest portion of the water jacket. If the water does not drain out from the water jacket, then mold, mildew or other growth can occur leading to contamination of the incubator 100. The operator has to bend down and manually turn the drain cap 195 in an awkward left-handed direction to remove the drain cap. Injuries can occur while opening the drain cap 195, such as back pains, should the operator not bend down properly, injuries to the hand and fingers should the drain cap 195 be stuck and difficult to rotate open. These injuries increase costs to the employers of the operator. Additionally, the operator (who can be a researcher) can require downtime to recover from the injuries and thus, important experiments may be delayed.

Therefore, there is a need for an apparatus and method to drain liquids from a water jacketed incubator that does not require the operator to bend down and perform an awkward maneuver. Additionally, there is a need for an incubator that can drain liquids from the water jacket without causing injuries to the operator.

SUMMARY OF THE INVENTION

The present invention generally relates to an apparatus and method to drain liquids from a water jacketed incubator. An embedded control system is used to open and close the drain with a solenoid. The solenoid can open by actuating a switch or a control button on the user interface panel.

One embodiment of the present invention may include an evacuating apparatus for an enclosed chamber that includes an actuator mounted on an outer surface of the enclosed chamber, a water jacket that can be filled with a liquid surrounds an inner chamber of the enclosed chamber, and an electronic valve that can allow liquids to drain from the water jacket, wherein the actuator can be in communication with the electronic valve. The actuator can be a switch or a control button. The evacuating apparatus can further include a controller that can be in communication with the actuator and can control when the actuator actuates the electronic valve. The electronic valve can be a solenoid and the actuator can be conveniently located for an operator. The controller with the actuator can actuate the electronic valve based on a period of time or an event and the electronic valve can be opened to allow liquid to evacuate from the water jacket.

In another embodiment, a method of evacuating liquids from an enclosed chamber can include providing a water jacket that can be filled with a liquid and surrounds an inner chamber of the enclosed chamber, actuating an actuator positioned outside of the enclosed chamber, and evacuating liquids from the water jacket through an electronic valve that is in communication with the actuator. The electronic valve may be a solenoid and the actuator is a switch or a control button. Additionally, evacuating the liquids can be opening the electronic valve to allow liquid to evacuate from the water jacket and actuating the actuator may be accomplished by a controller that can be in communication with the actuator. The method of evacuating liquids from an enclosed chamber of claim 14, wherein the controller with the actuator can actuate the electronic valve based on a period of time or an event.

In still another embodiment, an evacuation system for an enclosed chamber can include a means for actuating mounted on an outer surface an enclosed chamber means, a means for containing liquids that surrounds an inner chamber means of the enclosed chamber means, and a means for electronically releasing liquids from the inner chamber means, wherein the means for actuating and the means for electronically releasing fluids are in communication with each other. The means for actuating can be selected from a switch, other actuating devices, a control button or a combination thereof. The means for electronically releasing fluids may be a solenoid. The evacuation system for an enclosed chamber can further include a means for controlling that can actuate the means for actuating and is in communication with the means for actuating and the means for electronically releasing. The means for controlling with the means for actuating can actuate the electronic valve means based on a period of time or an event.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The present invention allows an operator to drain liquids from a water jacketed of an incubator via a switch or a control button. Because the switch or control button can be located in a convenient place on the outside of the incubator, the operator does not have to bend down and complete an awkward maneuver to open the drain.

Figure 1:
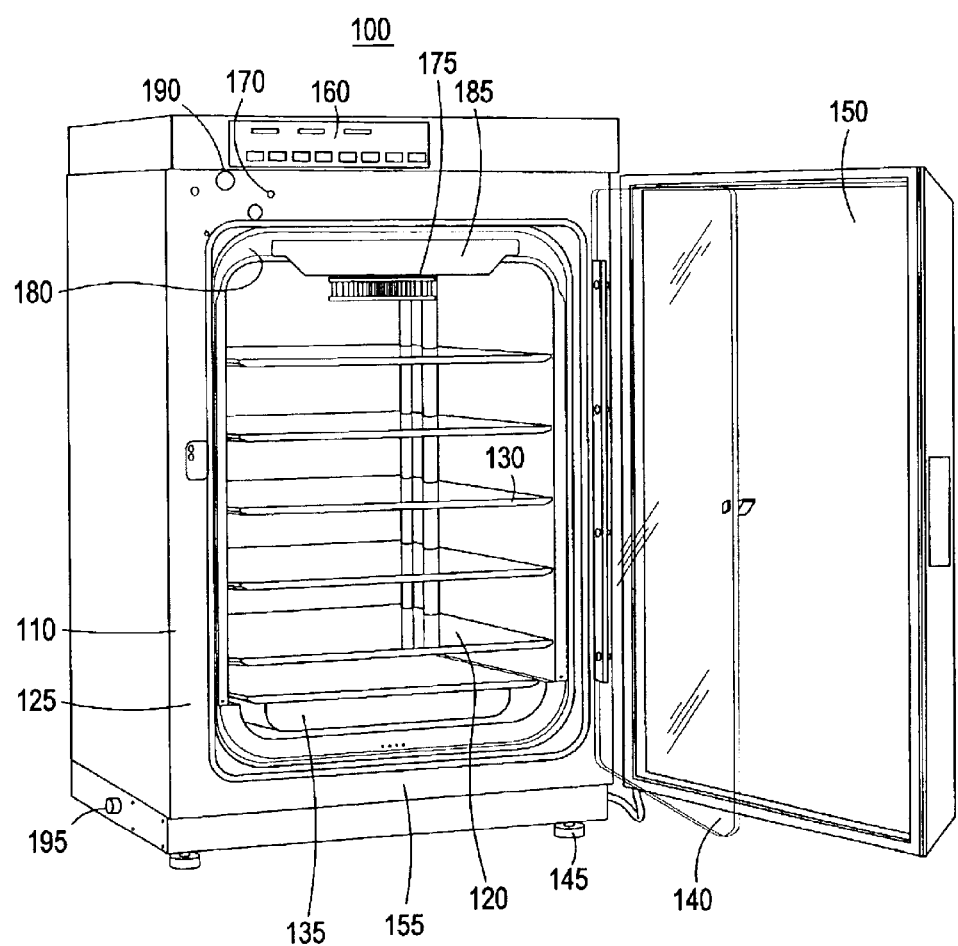
FIG. 1 is a perspective view of a water jacketed incubator.
Figure 2A:
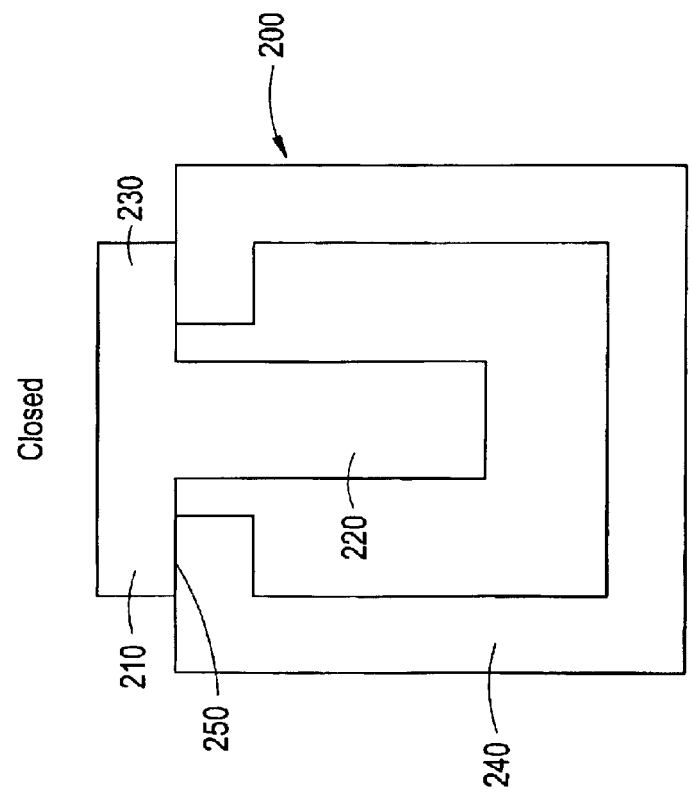
FIG. 2A and FIG. 2B illustrates an embodiment of a solenoid of the present invention.
Figure 2B:
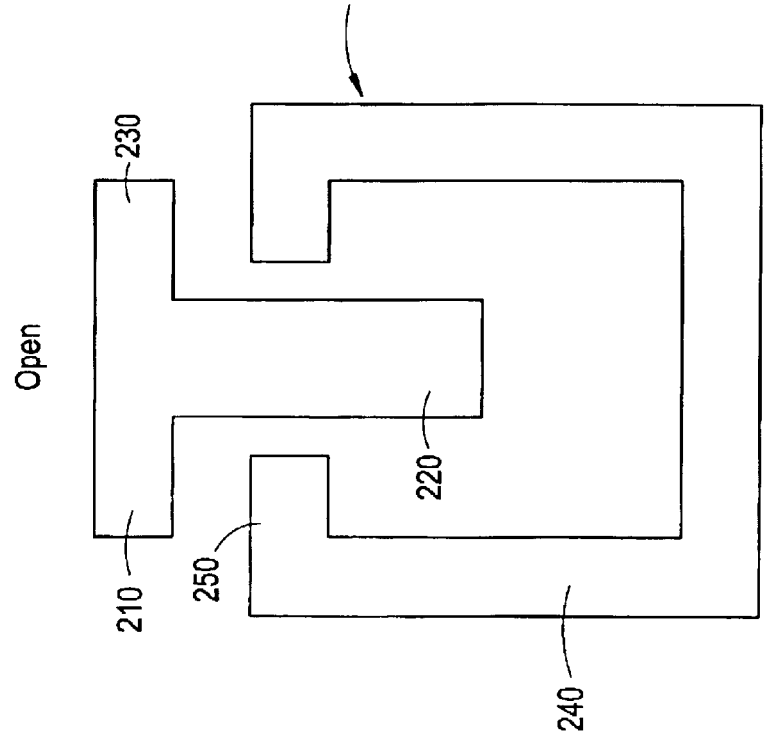

FIG. 2A and FIG. 2B illustrates an embodiment of a solenoid 200 of the present invention. In one embodiment of the invention, the solenoid 200 can be used to drain the liquid from the water jacket. In FIG. 2A, the solenoid is shown in the open position. The solenoid 200 is an electromagnet that includes a coil 240 and a plunger 210. The coil 240 is made up of many "C" stacks, which when current flows through it, creates a magnetic field. The C stacks helps to concentrate the magnetism where it is desired.

The plunger 210 has an upper portion 230 and a lower portion 220. The upper portion 230 can provide a seal with an upper surface 250 of the coil 240. The plunger 210 is typically made from iron (or other conductive material) because it is an excellent conductor. Normally, the plunger 210 is "repelled" from the coil 240 due to the magnetic field of the coil being the same magnetic sign as the plunger (both can be positive). The plunger 210 is "pulled in" when current passes through the coil 240 and the polarity of the coil's magnetic field is reversed (see FIG. 2B). Because the plunger 210 is in the opened position, the plunger allows fluids to pass through it.

In FIG. 2B, the solenoid 200 is shown in the closed position. Current is applied to the coil 240, causing the change in the polarity of the magnetic field (change to negative) of the coil. Because the polarity has changed in the coil 240, the plunger 210 (being positive) and the upper portion 230 are "pulled in" towards the coil 240. The upper portion 230 creates a tight seal with the upper surface 250. The seal does not allow any liquids to flow through the solenoid 200.

Figure 3:
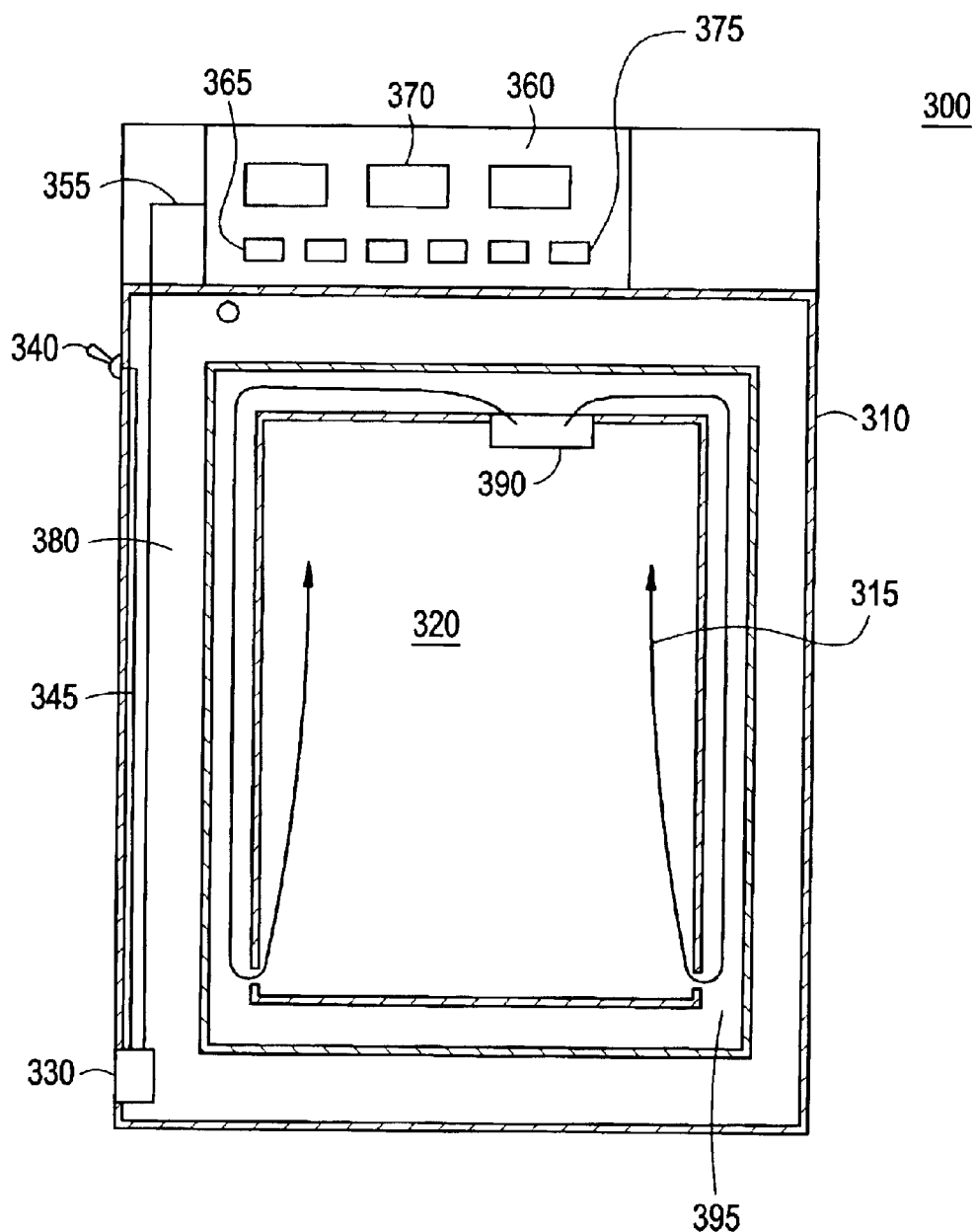
FIG. 3 illustrates the incubator with the solenoid.

FIG. 3 illustrates the incubator 300 with the solenoid 330. In one embodiment of the invention, the incubator 300 includes a cabinet 310 having an interior chamber 320. The cabinet includes a control system 360 having at least one or more display 370 and a user interface 365. The control system 360 can control all aspects and operating parameters of the incubator 300 through a microprocessor.

The process as described herein may be controlled by one of any form of general purpose computer processor that can be used in an industrial setting for controlling various chambers and incubators. The control system 360 may use any suitable microprocessor, memory, such as random access memory, read only memory, floppy disk drive, hard disk, or any other form of digital storage, local or remote. Various support circuits may be coupled to the control system 360 for supporting the processor in a conventional manner. Software routines as required may be stored in the memory or executed by a second control system that is remotely located.

The control system 360 can control the operating temperature of the incubator 300 by monitoring the temperature in the interior chamber 320 and controlling the heater (not shown). The control system 360 can also control the gas levels in the interior chamber 320, such as the $CO_2$ level and the $O_2$ level, by monitoring and controlling the amount and type of gas that is injected into the interior chamber. The control system 360 also includes one or more displays 370, which includes visual and audible information. The displays 370 can provide information such as door open, current gas levels, setpoints of the gases, the temperature, humidity level and other useful information. The control system 360 also includes a control button 375, which can electronically actuate a solenoid 330.

The solenoid 330 is preferably located near the bottom or at a point where a liquid in a water jacket 380 can fully or most fully drain from the jacket. The solenoid 330 can also be the type previously described above. It is important to drain as much of the water from the water jacket 380, as possible, so that unwanted growth does not occur. The solenoid 330 is in communication with the control system 360 via a wireline 355. The wireline 355 can provide a communication link and/or power to the solenoid 330. The control button 375 is in communication with the control system 360, which together can actuate the solenoid 330 to open and close. When the operator desires to empty the liquid from the water jacket 380, he can actuate the solenoid 330 with the control button 375. When the solenoid 330 is actuated, the solenoid 330 can open and release the liquid in the water jacket 380. As stated above, the solenoid 330 is open because the polarity of the solenoid changed (due to current being shut-off) causing the plunger to be repelled from the solenoid. The control system 360 can keep the solenoid 330 open until the operator again actuates the solenoid with the control button to close it. The solenoid 330 closes because the polarity of the solenoid was changed when current was introduced and pulled in the plunger 210 causing it to seal with the solenoid.

Alternatively, the control system 360 can keep the solenoid open for a predetermined period of time or for a period of time in which the liquid can fully evacuate from the water jacket 380. By having the actuating button 375 conveniently located as part of the control system, the operator can easily actuate the solenoid without having to bend over and unscrew or turn the drain cap to evacuate the liquid. Thus, injuries to the operator can be avoided and the experiments are not interrupted.

In an alternate embodiment, the control button 375 is in direct communication with the solenoid 330 and can actuate it without the assistance of the control system 360. The solenoid 330 is for exemplary purposes only and other devices performing the same function of the solenoid can be used in the embodiments of the invention. Although a solenoid is shown herein as an example of an electronic valve, any electronic valve that opens and closes so that liquids can be evacuated from the water jacket can be used. The solenoid is preferably an electronic solenoid, however, other type of solenoids can also be used.

In another embodiment, the control system 360 can be programmed to open and close the solenoid 330. The control system 360 can be programmed to open and evacuate the liquids from the water jacket 380 on a set of period of time, after or before an event occurs, or other parameters desired by the operator. The period of time can be every hour, everyday, every other day, once a week, every other week, at the end of a shift so the incubator can dry overnight, at every maintenance period, or any other period that is desired by the operator. The solenoid can be actuated after an event, such as before the first batch is run, after or before the last batch of samples are run or after or before two batches are run, after or before three batches are run or after or before any other events desired by the operator. By having the control system 360 automatically actuate the solenoid at a time period or after or before an event, the operator can have more time to do other things, such as preparing the samples to be run.

In still another embodiment, a switch 340, such as a toggle switch, can be used to actuate the solenoid 330. The switch is in communication with the solenoid 330 via a wireline 345. Similar to wireline 355, wireline 345 can provide a communication link and/or power to the solenoid 330. The switch can actuate the solenoid to the open position and allows liquid to escape from the water jacket 380. In operation, the switch can be "thrown" by the operator by moving in a first direction (cutting off the current) and actuating the solenoid 330 to open. The solenoid 330 can remain open until the switch is moved in a second direction (allowing current to flow) causing the solenoid to close. The switch, like the actuating button, being located in a convenient location in order to reduce injuries to the operator.

The switch 340 and the control button 375 can be located anywhere on the incubator. Preferably, the switch and button are located where it is convenient to the operator, such as shoulder level, or where the operator does not have to bend down in order to reach it. The solenoid can have a self-contained power source so that the switch and button acts like a current gate to allow the current to flow or cut it off. The switch 340 and the control button 375 can be replaced by other devices that can turn the solenoid on and off.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An evacuating apparatus for an enclosed chamber, comprising:
    an actuator mounted on an outer surface of the enclosed chamber;
    a water jacket that can be filled with a liquid surrounds an inner chamber of the enclosed chamber; and
    an electronic valve that allows liquids to drain from the water jacket, wherein the actuator is in communication with the electronic valve.

2. The evacuating apparatus of claim 1, wherein the actuator is a switch.

3. The evacuating apparatus of claim 1, wherein the actuator is a control button.

4. The evacuating apparatus of claim 1, further including a controller that is in communication with the actuator and controls when the actuator actuates the electronic valve.

5. The evacuating apparatus of claim 1, wherein the electronic valve is a solenoid.

6. The evacuating apparatus of claim 1, wherein the actuator is conveniently located for an operator.

7. The evacuating apparatus of claim 4, wherein the controller with the actuator can actuate the electronic valve based on a period of time or an event.

8. The evacuating apparatus of claim 1, wherein the electronic valve can be opened to allow liquid to evacuate from the water jacket.

9. A method of evacuating liquids from an enclosed chamber, comprising:
    providing a water jacket that can be filled with a liquid and surrounds an inner chamber of the enclosed chamber;
    actuating an actuator positioned outside of the enclosed chamber; and
    evacuating liquids from the water jacket through an electronic valve that is in communication with the actuator.

10. The method of evacuating liquids from an enclosed chamber of claim 9, wherein the electronic valve is a solenoid.

11. The method of evacuating liquids from an enclosed chamber of claim 9, wherein the actuator is a switch.

12. The method of evacuating liquids from an enclosed chamber of claim 9, wherein the actuator is a control button.

13. The method of evacuating liquids from an enclosed chamber of claim 9, wherein evacuating the liquids is opening the electronic valve to allow liquid to evacuate from the water jacket.

14. The method of evacuating liquids from an enclosed chamber of claim 9, wherein actuating the actuator is accomplished by a controller that is in communication with the actuator.

15. The method of evacuating liquids from an enclosed chamber of claim 14, wherein the controller with the actuator can actuate the electronic valve based on a period of time or an event.

16. An evacuation system for an enclosed chamber, comprising:
- a means for actuating mounted on an outer surface an enclosed chamber means;
- a means for containing liquids that surrounds an inner chamber means of the enclosed chamber means; and
- a means for electronically releasing liquids from the inner chamber means, wherein the means for actuating and the means for electronically releasing fluids are in communication with each other.

17. The evacuation system for an enclosed chamber of claim 16, wherein the means for actuating can be selected from a group consisting of a switch, other control means, a control button and a combination thereof.

18. The evacuation system for an enclosed chamber of claim 16, wherein the means for electronically releasing fluids is a solenoid.

19. The evacuation system for an enclosed chamber of claim 16 further comprising a means for controlling that can actuate the means for actuating and is in communication with the means for actuating and the means for electronically releasing.

20. The evacuation system for an enclosed chamber of claim 19, wherein the means for controlling with the means for actuating can actuate the electronic valve means based on a period of time or an event.

* * * * *